(12) United States Patent
Thomas

(10) Patent No.: US 12,290,457 B2
(45) Date of Patent: May 6, 2025

(54) PHOTON-ACTIVATABLE GEL COATED INTRACRANIAL STENT AND EMBOLIC COIL

(71) Applicant: Jeffrey E. Thomas, Hillsborough, CA (US)

(72) Inventor: Jeffrey E. Thomas, Hillsborough, CA (US)

(73) Assignee: Jeffrey E. Thomas, Hillsborough, CA (US)

( * ) Notice: Subject to any disclaimer, the term of this patent is extended or adjusted under 35 U.S.C. 154(b) by 1021 days.

(21) Appl. No.: 17/181,537

(22) Filed: Feb. 22, 2021

(65) Prior Publication Data

US 2021/0196487 A1   Jul. 1, 2021

Related U.S. Application Data

(62) Division of application No. 15/310,334, filed as application No. PCT/US2015/030386 on May 12, 2015, now Pat. No. 10,959,865.

(Continued)

(51) Int. Cl.
*A61F 2/90* (2013.01)
*A61B 17/12* (2006.01)
(Continued)

(52) U.S. Cl.
CPC .......... *A61F 2/90* (2013.01); *A61B 17/12031* (2013.01); *A61B 17/12113* (2013.01);
(Continued)

(58) Field of Classification Search
CPC .................. A61F 2/90; A61F 2002/823; A61F 2250/0001; A61F 2250/0015;
(Continued)

(56) References Cited

U.S. PATENT DOCUMENTS 5,803,895 A * 9/1998 Kronholz ............. A61N 5/1007
                                                                  600/3
6,296,603 B1   10/2001 Turnlund et al.
(Continued)

FOREIGN PATENT DOCUMENTS

| | | |
|---|---|---|
| JP | 2001509412 A | 7/2001 |
| JP | 2004535868 A | 12/2004 |

(Continued)

OTHER PUBLICATIONS

Chai, Qinyuan et al.; "Hydrogels for Biomedical Applications: Their Characteristics and the Mechanisms behind Them"; Gels; Jan. 24, 2017; pp. 6-20; vol. 3, Issue 1, MDPI.

(Continued)

*Primary Examiner* — Tan-Uyen T Ho
*Assistant Examiner* — Chima U Igboko
(74) *Attorney, Agent, or Firm* — ARENTFOX SCHIFF LLP

(57) ABSTRACT

An intracranial stent includes a proximal end, a distal end, and a tubular sidewall extending there between and a patch covering at least a portion of the sidewall; wherein the patch is capable of diverting blood flow past the neck of an intracranial aneurysm. The patch may be made of a photon-activatable material or a tightly woven metal material with a density greater than a density of the sidewall itself.

20 Claims, 4 Drawing Sheets

Related U.S. Application Data

(60) Provisional application No. 62/058,847, filed on Oct. 2, 2014, provisional application No. 61/991,693, filed on May 12, 2014, provisional application No. 61/991,688, filed on May 12, 2014.

(51) Int. Cl.
    *A61B 17/00*     (2006.01)
    *A61B 90/00*     (2016.01)
    *A61F 2/82*     (2013.01)

(52) U.S. Cl.
    CPC .... *A61B 17/12118* (2013.01); *A61B 17/1214* (2013.01); *A61B 17/12181* (2013.01); *A61B 2017/00084* (2013.01); *A61B 2017/005* (2013.01); *A61B 2090/3966* (2016.02); *A61F 2002/823* (2013.01); *A61F 2250/0001* (2013.01); *A61F 2250/0015* (2013.01); *A61F 2250/0023* (2013.01)

(58) Field of Classification Search
    CPC ....... A61F 2250/0023; A61B 17/12031; A61B 17/12113; A61B 17/12118; A61B 17/1214; A61B 17/12181; A61B 2017/00084; A61B 2017/005; A61B 2090/3966
    See application file for complete search history.

(56) References Cited

U.S. PATENT DOCUMENTS

| | | | |
|---|---|---|---|
| 8,470,013 | B2 | 6/2013 | Duggal et al. |
| 8,715,340 | B2 | 5/2014 | Rudakov et al. |
| 2001/0049464 | A1* | 12/2001 | Ganz ................ H01J 35/32 600/3 |
| 2003/0040771 | A1 | 2/2003 | Hyodoh |
| 2003/0060782 | A1 | 3/2003 | Bose |
| 2005/0033409 | A1* | 2/2005 | Burke ............... A61B 17/1219 623/1.15 |
| 2005/0142163 | A1* | 6/2005 | Hunter .................... A61P 19/00 424/423 |
| 2005/0267570 | A1* | 12/2005 | Shadduck ........ A61B 17/12022 623/1.44 |
| 2006/0200230 | A1 | 9/2006 | Richter |
| 2007/0135803 | A1* | 6/2007 | Belson ............... A61B 1/00154 606/1 |
| 2007/0135907 | A1* | 6/2007 | Wilson ...................... A61F 2/95 623/1.44 |
| 2007/0225564 | A1* | 9/2007 | Couvillon, Jr. ........ A61B 1/012 600/128 |
| 2010/0106240 | A1* | 4/2010 | Duggal .................... A61F 2/91 623/1.15 |
| 2010/0131002 | A1 | 5/2010 | Connor et al. |
| 2010/0286758 | A1 | 11/2010 | Berglund |
| 2011/0190695 | A1* | 8/2011 | Thilwind .............. A61M 1/064 604/74 |

FOREIGN PATENT DOCUMENTS

| | | |
|---|---|---|
| JP | 2005075986 A | 3/2005 |
| JP | 2005177488 A | 7/2005 |
| JP | 2007530213 A | 11/2007 |
| JP | 2009513288 A | 4/2009 |
| JP | 2012504450 A | 2/2012 |
| JP | 2012524620 A | 10/2012 |
| WO | 9902092 A1 | 1/1999 |
| WO | 0200139 A1 | 1/2002 |
| WO | 02071994 A1 | 9/2002 |
| WO | 02087449 A1 | 11/2002 |
| WO | 03007823 A1 | 1/2003 |
| WO | 2007051179 A2 | 5/2007 |
| WO | 2014028913 A1 | 2/2014 |

OTHER PUBLICATIONS

Yang, Ting, Ph.D.; "Mechanical and Swelling Properties of Hydrogels"; Ph.D. Thesis, KTH Chemical Science and Engineering; 2012; Wiley Periodicals, Inc.

Guirez, Syed K. H. et al.; "Hydrogels: Methods of Preparation, Characterisation and Applications"; Progress in Molecular and Environmental Bioengineering—From Analysis and Modeling to Technology Applications; Aug. 1, 2011; pp. 117-150; Intech.

Simoes, Susana et al.; "Modular Hydrogels for Drug Delivery"; Journal of Biomaterials and Nanobiotechnology; Apr. 2012; pp. 185-199; vol. 3; SciRes.

Khoylou, F and F. Naimian; "Radiation synthesis of superabsorbent polyethylene oxide/tragacanth hydrogel"; Radiation Physics and Chemistry; 2009; pp. 195-198; vol. 78; Elsevier Ltd.

Extended European Search Report dated Dec. 6, 2017 in related European Patent Application No. 15793105.6 filed May 12, 2015; 7 pages.

Office Action issued in JP Application No. 2016-566730, dated Feb. 26, 2019.

Office Action issued in Japanese patent application No. 2016-566730, dated Aug. 14, 2019.

Pre-trial Examination issued in JP Patent Application No. 2016-566730, dated Apr. 1, 2020.

\* cited by examiner

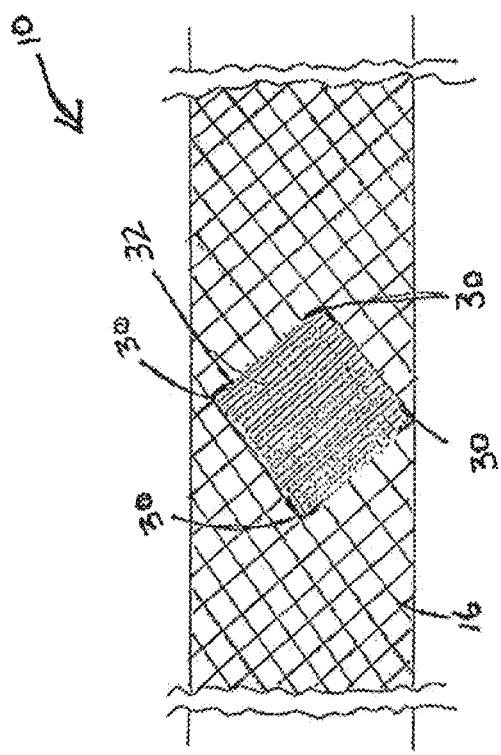

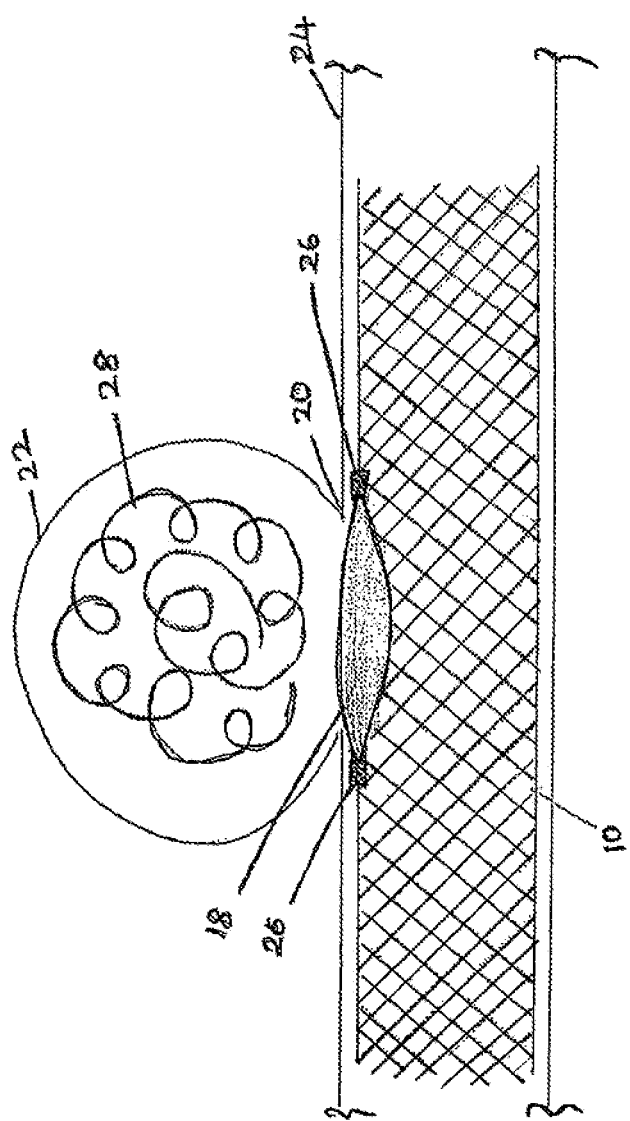

PHOTON-ACTIVATABLE GEL COATED INTRACRANIAL STENT AND EMBOLIC COIL

RELATED APPLICATIONS

This application claims priority to and is a divisional application of U.S. patent application Ser. No. 15/310,334 filed Nov. 10, 2016 and titled "Photon-Activatable Gel Coated Intracranial Stent and Embolic Coil," which is a national stage entry of PCT Patent Application No. PCT/US15/30386 filed May 12, 2015 and titled "Photo-Activatable Gel Coated Intracranial Stent and Embolic Coil," which claims priority to U.S. Provisional Patent Application No. 61/991,693 filed May 12, 2014 and titled "Embolic Coil Delivery System and Method of Using Same," U.S. Provisional Patent Application No. 61/991,688 filed May 12, 2014 and titled "Photoactivatable Gel Coated Intracranial Stent," and U.S. Provisional Application No. 62/058,847 filed Oct. 2, 2014 and titled "Photoactivatable Gel Coated Intracranial Stent and Embolic Coils." The entire contents of each of these applications are incorporated herein by reference.

FIELD OF INVENTION

The present disclosure generally relates to stents, embolic devices and methods of their use in treating intracranial aneurysms. Specifically, the disclosure relates to an intracranial stent with an outer wall that is at least partially covered with a photon-activatable gel.

BACKGROUND OF THE INVENTION

Endovascular treatment of a cerebral aneurysm is currently carried out using either embolic substances or devices delivered inside the aneurysm, such as coils or liquid embolic agents, or by diverting blood from the orifice of such an aneurysm by placing an intravascular stent across the orifice. In the former case, it is desirable to employ a device or substance that takes up as much space inside the aneurysm as possible, simultaneously excluding blood and facilitating thrombosis. In the latter case, it is desirable to use a device that mimics or reconstructs the vascular wall, and in so doing most effectively prevents blood in the normal vascular lumen from penetrating the stent and entering the orifice of the target aneurysm. This goal is accomplished by using a stent with smaller fenestrations, or more metal density for a given surface area.

It is also desirable, in the case of intracranial blood vessels, known to be supremely fragile and tortuous, to utilize a stent with the greatest flexibility and navigability possible, in order to minimize damage to the highly sensitive endothelium of such vessels. As the properties of flow diversion (accomplished with smaller fenestrations, or greater metallic density per unit area of vessel wall) and atraumatic navigability/flexibility (usually accomplished with pliable materials and larger fenestrations, or lesser metal: vessel wall surface area) are at odds, it would be desirable, for the purpose of flow diversion or intracranial vascular reconstruction, to employ a stent characterized by flexibility and navigability, that is subsequently transformed by a chemical process once it is in position, into a device with smaller fenestrations and less permeability.

SUMMARY OF THE INVENTION

Devices such as an intracranial stent, an embolic coil and methods of using such devices in a coil embolization procedure of treating cerebral aneurysm is disclosed.

An intracranial stent may include a proximal end, a distal end, and a tubular sidewall extending there between and a patch covering at least a portion of the sidewall; wherein the patch is capable of diverting blood flow past the neck of an intracranial aneurysm. The patch may be composed of or coated with a photon-activatable gel material or a tightly woven metal material with a density greater than a density of the sidewall itself. When the patch is covered by a photon-activatable gel, it may be activated by sources selected from the group comprising light emitting diodes (LED), quartz, tungsten-halogen, xenon-plasma, x-ray photon and the like. In one embodiment the photon-activatable gel may be activated by x-ray photon. Once activated the photon-activatable gel may expand to an extent that it may cover the aneurysm orifice in such a way that a complete diversion of the blood flow past the neck of the aneurysm is achieved. The radial expansion of the gel however may not significantly alter the dimensions of the adjacent normal vessel wall. The photon-activatable gel coated stent of this embodiment may thus be suitable for coil embolization of a cerebral aneurysm.

In another embodiment an embolic coil suitable for delivery into an aneurysm cavity may be completely or partially covered by a photon-activatable gel patch. In this embodiment when the photon-activatable gel is activated by a photon source such as x-ray, the embolic coil may undergo physical transformation in situ. The transformation may also be chemical and accompanied with release of heat or photochemical to become a tissue irritant or toxic substance causing local and segmented injury thus leading to a complete or partial occlusion of the aneurysm cavity. Consequently, the aneurysm cavity may be totally isolated from the original and natural circulation.

The stent delivery system described and claimed below incorporate the necessary structural modifications and features needed to provide the desired handling characteristic of an intracranial stent or coil delivery system. For the most part, they are designed with a radially expanding stent in mind, but they will prove useful in applications of balloon expanding or shape memory stents. Due to the presence of the photon-activatable gel on the stent and embolic coils, it is important to prevent premature activation of the gel. As a measure to avoid that, the distal tip of the delivery catheter may be composed of a radiation dense substance, such as tungsten or lead, to effectively prevent contact of x-ray photons with the activatable portion until desired.

BRIEF DESCRIPTION OF DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

FIG. 3 is a perspective view of one embodiment of an intracranial stent with an increased density in its side wall.

FIG. 4 is a perspective view of one embodiment of an intracranial stent used with coated embolic coil during a typical embolization procedure.

DETAILED DESCRIPTION

Intracranial stents may be used to provide support at the neck of an aneurysm in order to allow remodeling of the parent artery by providing a scaffold that promotes endothelial repavement, excluding the aneurysm from the original, and natural circulation of the patient's blood.

Figure 1:
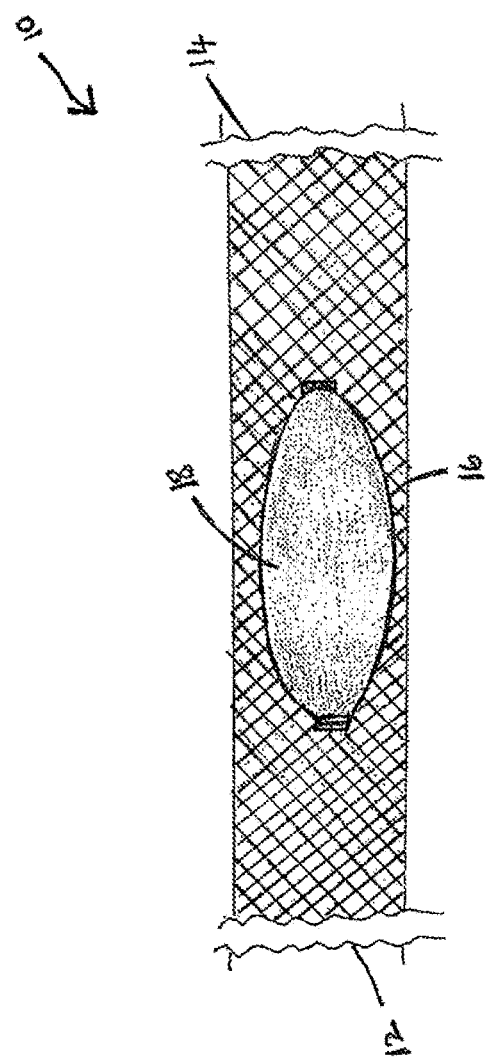
FIG. 1 is a perspective view of one embodiment of an intracranial stent partially covered with a photo-activatable gel.

As shown in FIG. 1, in one embodiment, a stent 10 may include a distal end 12, a proximal end 14, and a tubular sidewall 16 extending there between. Generally, the stent 10 is tubular, fenestrated, or braided and may be of varying dimensions depending on the anatomy of the blood vessels for which they are intended. For intracranial stents, they may generally be about 4 mm on either side of the aneurysm orifice, so that a total of 8 mm of stent length is added to the width of the aneurysm orifice. The general length of the stent may therefore range from about 4 mm to about 16 mm. The width or thickness of the stent 10 may span from about 3 mm to about 8 mm. In some embodiments, a stent 10 of thickness of about 2.5 mm in diameter may be used for larger peripheral vessels or aorta. The stent 10 may be made of any suitable material, such as a metal or polymer. It may be comprised of a loosely woven metal material that is flexible enough to be navigable through the small arterial vessels in the brain. The stent 10 may be composed of a single material or a combination of materials. Importantly, the material of which the stent is made allows for radial expansion of the stent inside the blood vessel. For instance, when the stent is loaded inside a microcatheter, the stent is in a compressed state. It may be manufactured according to either an open-cell (or 'open or expanded' state) or closed-cell (or 'closed or compressed' state) design but the common feature may be that the stent is folded under tension inside the microcatheter, and unfolds as the stent is liberated from the compressive influence of the microcatheter. Once unfolded, the stent 10 may expand to exert radial pressure from within the blood vessels. Before a neuro-interventional procedure, the stent 10 may be selected according to the size of the target blood vessels (width of the stent) in such a way as to assure that it continues to exert some degree of force after it is deployed. Hence, the selection of the length of the stent 10 accords to the aneurysm orifice width plus 8 mm, while the selection of the width of the stent accords to the inner diameter of the target vessel harboring the aneurysm, oversizing the stent width slightly for the vessel. Once the size of the stent is determined, the stent 10 may be placed in the neck of an aneurysm and expanded, as shown in FIG. 2.

Referring again to FIG. 1, the sidewall 16 of the stent 10 may be no more than partially covered by a photon-activatable gel material to form a gel patch 18. Any biologically compatible material or combination of materials that may be activated by photon sources or otherwise chemically activated are contemplated as suitable for coating the side-wall portion of the stent to form a gel patch 18. Expansion of the gel patch 18 thus represents a physical transformation of the stent 10. It may be appreciated by those skilled in the art that expansion of the gel patch 18 may close the interstices and may effectively reduce the size of each fenestration covered by the gel patch 18. Hence, stent 10 which may be more porous before gel activation may turn into a less porous device after activation of the gel patch 18. Unlike many other intracranial stents, the gel patch 18 may cover only a portion of the sidewall 16 of the stent 10 to provide a thickness or density sufficient to completely divert blood flow past the neck of the aneurysm 20. By coating only a portion of the sidewall 16, the remainder of the stent 10 may be composed of a loosely woven material, promoting flexibility and maneuverability through the delicate vessel. In addition, by coating only a portion preferably mid portion of the stent with photon-activatable gel, its actual contact with the adjacent normal blood vessel wall may be minimized. The coated portion of the stent when activated may therefore serve to exclude the aneurysm from the normal blood flow and make the stent function as a true flow diversion device. When the stents are manufactured, the length of the coating may be varied and stents may be supplied according to the expected frequency of a given size of aneurysm orifice. Oversizing this central region, in comparison to the width of the aneurysm orifice, would be expected to have a minimal effect. Accordingly, a small degree of overlap (2-4 mm) with normal vessel wall would be acceptable. In some embodiments, such overlap is desirable to minimize the hemodynamic impact of a junctional discordance close to the aneurysm as any little turbulence caused by a flow-diverting stent can potentially lead to high rupture rate of previously un-ruptured aneurysms.

Figure 2:
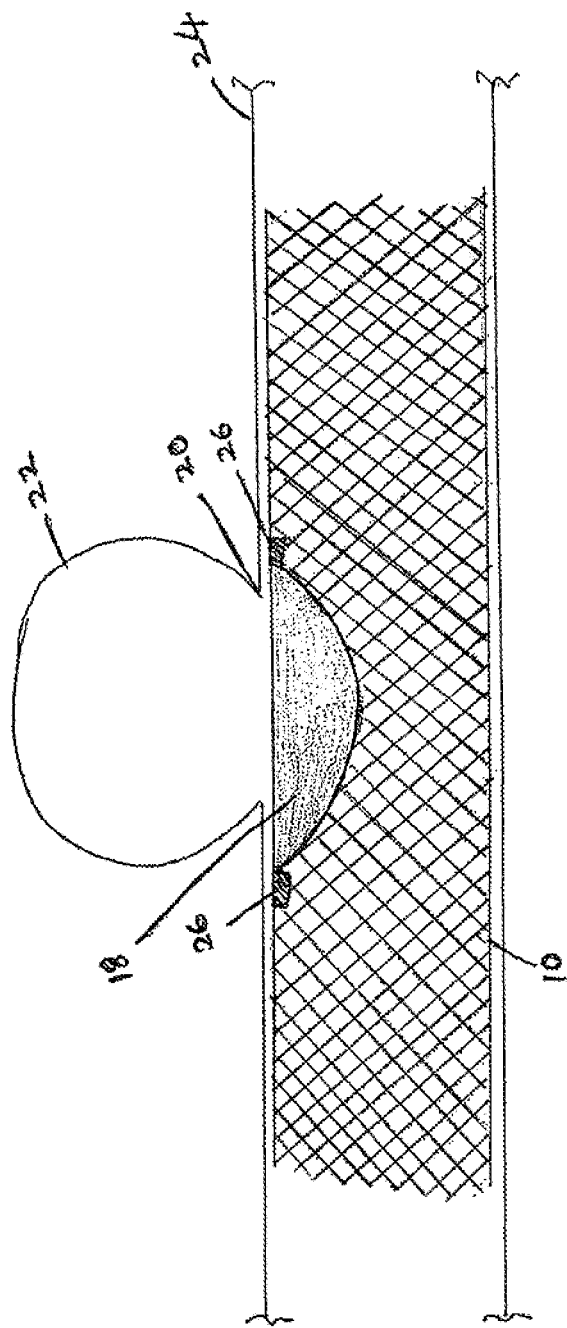
FIG. 2 is a perspective view of the intracranial stent of FIG. 1 disposed within an intracranial vessel.

As shown in FIG. 2, once placed in a vessel 24, the stent 10 may be unfolded from 'a closed or compressed' state to an 'open or expanded' state by a balloon or other suitable device. The 'open' stent 10 may be positioned in the target site of the blood vessel in such a way that the photon-activatable gel patch 18 extends across the neck 20 of the aneurysm 22 to approximately cover the width of the aneurysm orifice. A digital measurement of the aneurysm orifice dimensions may be performed using angiography. To determine the correct placement of the gel patch 18 across the aneurysm orifice, radiopaque markers 26 may also be disposed at or along the perimeter of the patch 18. After the stent 10 is deployed at the target region by pushing it out of the delivery microcatheter and unfolded, the photon-activatable gel patch 18 may then be activated by exposing it to a light-emitting diode (LED), or another light source, such as quartz-tungsten-halogen or xenon plasma or x-ray photon. The use of the term "activation" should be understood to mean that the patch is polymerized, expanded, hardened, or otherwise altered to achieve a desired effect. The energy of the light source may be appropriate for activating the gel and initializing polymerization. As such, the light source should be sufficient to account for the medium, i.e. blood, in which is it activated. A microcatheter, or suitable delivery system (not shown), may be used to deploy the light source to the gel patch 18. In embodiments where the activation of the photon-activatable gel is by x-ray photon, the distal tip of the delivery microcatheter is designed to carry a radiation-shielding element to prevent premature activation of the photon-activatable gel in the stent. The element may be composed of a radiation-dense substance, such as tungsten or lead, to effectively prevent contact of x-ray photons with the activatable portion until desired. The dimension of the radiation-shielding element would be such that it may substantially cover the gel patch 18 of the stent. Preferably, the radiation-shielding element may cover the mid portion of the stent which is coated by the photon-activatable gel and the distal portion of the uncoated stent. This latter design ensures that the operator has sufficient time to deploy the stent without premature activation or to withdraw the activatable portion of the stent in the event of erroneous targeting/deployment. Use of x-ray photon to activate the gel also has the additional advantage of making use of the means of routine imaging (x-ray fluoroscopy) during the neuro-interventional procedure. Activation of the gel patch 18 by the x-ray photon causes the gel to expand so that the entire width of the aneurysm orifice is covered by the gel patch 18.

The activation of the gel patch 18 on the stent 10 results in gel expansion by about several hundred percent and preferably at least about 25% to at least about 100%. The exposure time to activate the gel substance may depend on the nature of the substance used and may generally range from at least about 1 minute to about 10 minutes. In some instances, the photo-activation is allowed until the expansion of gel is sufficient to allow the gel patch 18 to completely cover the aneurysm neck. It may be that the photon-activation of the gel patch 18 on the stent 10 may result in at least about 100% expansion of the gel resulting in complete sealing of the aneurysm orifice.

To determine whether the expansion of the gel results in total occlusion of the aneurysm orifice, it is also possible to calculate or make an educated guess based on the general degree of expansion of the gel in addition to the un-activated fenestration size to determine the appropriate fenestration size reliably associated with complete occlusion. In some instances this is already known generally or for specific existing stents. For the stent 10, the ultimate size of the stent fenestrations would be determined generally in the pre-clinical lab. Overlapping metallic stents, and high density stents like the Pipeline, reliably cause more flow diversion as the metal:artery ratio increases. This is a function of increasing the density or solidness of the stent. The ultimate stent would be solid, but this cannot be done in the brain because of the necessity of navigation. Hence by using a gel covered patch 18, a generally porous and easily navigable stent 10 may be converted upon photon-activation into a relatively less porous and rigid stent (compared to the flexibility before activation) that cannot easily navigate through the tortuous cerebral vasculature.

As shown in FIG. 3, in another embodiment, instead of a patch made of a photon-activatable gel, a patch 32 may be made by increasing the density of the metal weaving in discrete areas of the sidewall 16. Like the photon-activatable gel patch 18 (shown in FIGS. 1,2 and 4), the woven patch 32 may include radiopaque markers 30 at or along its perimeter to allow the physician to place the patch 32 at the neck of the aneurysm. Also, because the density is increased over only a small portion of the sidewall 16, the stent 10 may be more easily navigated through the vessels of the brain than a uniformly densely woven intracranial stent.

In another embodiment a physician may also use a stent in combination with an embolic coil 28, as shown in FIG. 4. Similar to the stent 10, the embolic coil 28 may be coated completely or partially with the photon-activatable gel substance and placed within the aneurysm cavity using known procedures. The placement of photon-activatable gel coated embolic coil may be accomplished through the wall of the stent, where the stent is slightly perforate (with a high metal to vessel wall ratio) or where the coil may be pushed into the aneurysm through slots in the wall of an imperforate stent 10. Visualization of the coil placement within the aneurysm cavity may be achieved by placing radiopaque markers on the coil 28. After deployment of the gel coated coil 28 in the aneurysm cavity, the gel may be activated with a photon source. Upon activation, the gel substance may cause expansion of the coil and/or promote chemical or photochemical transformation in situ eventually causing coagulation and clotting within the aneurysm. To ensure immediate isolation of the aneurysm from the blood vessel, and to ensure that coils do not escape the wide aneurysm sac, a typical intracranial stent may be deployed immediately after or before the placement of the coils.

In another embodiment, an embolic coil 28 (shown in FIG. 4) may also be coated with gel substances that are capable of undergoing chemical transformation. In this embodiment when the coil is deployed within the aneurysm cavity the gel may be activated to trigger a chemical transformation that releases heat instead of (or) in addition to expansion of the gel by light or photon, as described above. The degree of the exothermic reaction required depends on the specific substance(s) selected, and the gel must be able to bond stably to the metallic coil or stent before and after activation. A reasonable exothermic reaction may result in the increase of temperature ranging from about 39° C. to about 45° C. In preferred embodiments, the temperature increase due to the exothermic reaction does not exceed 42° C., as any further increase can be injurious both to neurons and cerebral blood flow. To monitor the increase in temperature at the vicinity of the aneurysm one or more thermal sensors are placed at the distal end of the delivery microcatheter.

In yet another embodiment, the embolic coil coated with the gel 18 may manifest a photochemical transformation to a substance causing toxic vascular injury at the site of aneurysm with subsequent occlusion. In a preferred embodiment, the toxic vascular injury may be local and minimal with no detectable damage to adjacent healthy vascular tissue. To determine if gel expansion results in isolation of an aneurysm, angiography may be performed after activation. Typically, multiple angiographic runs are performed before, during, and after any neuro-interventional procedure to gauge the effect of an intervention on blood flow, both pathological and normal.

PROPHETIC EXAMPLES

Prophetic Example 1: Treating a Wide-Necked Cerebral Aneurysm

A patient presents to medical attention with a diagnosis of incidentally-discovered cerebral aneurysm of the internal carotid artery. The patient's angiogram demonstrates that the aneurysm has a wide neck, or orifice, to the parent vessel; therefore it is not amenable to simple coil embolization for fear that coils placed into the aneurysm will prolapse into the parent artery. The patient is also not an ideal candidate for craniotomy and clipping, for other reasons. One option for this patient would be a stent/coil technique, by which coils are deposited into a wide-necked aneurysm through an intracranial stent placed across the aneurysm neck. Although effective, this technique requires two procedures (deployment of intracranial stent, followed by deployment of coils), and this fact automatically doubles the surgical risk of the procedures. Also, being able to cross the stent with a microcatheter after it has been deployed, and then being able to deliver coils into the aneurysm beyond the stent, is not guaranteed to be possible, as the stent may be inadvertently moved by the second manipulation, and the angulation of the interstices of the stent may be unfavorable for crossing by the microcatheter. These problems could be avoided by the use of a single reconstructive device or the stent 10 of the present disclosure that includes a photon-activatable gel coated patch 18 configured to cover the orifice of the aneurysm, essentially reconstructing the defective portion of the arterial wall.

The photon-activatable gel coated stent of the present disclosure would allow the aneurysm to be excluded from the cerebral circulation without the need for additional coils. Although intracranial stents have been deployed for this purpose, they are usually ineffective at excluding blood flow from the aneurysm, because of excessive porosity. This same porosity is necessary because of the difficulty inherent in navigating the very fragile and tortuous cerebral vasculature. In order for the stent to be delivered safely to the intracranial location of the aneurysm, it must be flexible. In order for it to effectively exclude blood from the aneurysm, however, or from a damaged arterial wall segment, porosity must be minimized. This problem is solved by the photon-activatable gel coated stent 10, which is porous and flexible at the time of deployment, and is then transformed into a less-porous device by photon energy. This is accomplished by coating the stent with a gel that is activated to expand upon exposure to photon energy. One method of providing such energy is to use the angiographic X-ray equipment routinely used for endovascular procedures. Premature activation of the gel coating during intravascular navigation to the target is prevented because a short segment of radiation shielding is disposed at the end of the delivery microcatheter. The stent remains hidden from the radiation until it is pushed out from the microcatheter into its final position in the artery. Therefore, in a patient not ideally suited for simple coil embolization, clipping, or stent/coil technique; a fourth option can now be implemented with the photon-activatable gel coated stent 10.

To aid in placement of the stent 10, an angiographic map is created using dye injected through the parent vessel, and a roadmap image is created that demonstrates the exact location and configuration of the aneurysm. The stent is delivered across the aneurysm neck under fluoroscopy through the delivery microcatheter, which is navigated using a standard 0.014 microguidewire. The exact position of the stent is determined using fluoroscopic markers on the microcatheter and also on the stent itself. In this way it can be determined that the stent is accurately placed across the neck of the aneurysm. Once it is in position, it is held in place by a pusher wire that is lined up behind it within the microcatheter. The microcatheter is withdrawn as the pusher wire is stabilized; this results in the stent's being pushed out of the microcatheter into the artery at the desired location. As soon as the stent leaves the microcatheter, it is exposed to the ionizing photon radiation being used for visualization, and the polymerization of the coating begins. This photochemical transformation results in an expansion of the gel coating to several times its original thickness, effectively transforming the stent into a much less porous device that seals off the aneurysm orifice from the parent circulation. The reaction is complete within minutes. A control cerebral angiogram is performed immediately, demonstrating that the aneurysm no longer fills with blood and has been effectively excluded from the normal circulation. The procedure is concluded.

Prophetic Example 2. Treating a Site of Arterial Injury

A dissection is a tear in the arterial wall that allows blood from the lumen of the vessel to enter its muscular wall, expanding and causing stenosis of the residual lumen, or penetrating all layers of the vessel wall, allowing bleeding to occur into the subarachnoid space. A patient in this case arrives at the emergency room with symptoms of headache or stroke. Options for vascular repair include therapeutic occlusion of the involved vessel, direct surgical reconstruction, and endovascular repairs such as stent deployment. For an intracranial dissection, the same problem with navigation exists: a porous flexible reconstructive device is required for navigation of tortuous and fragile cerebral vasculature, but the effectiveness of the device at the target site is compromised by that same flexibility and high porosity that render it inferior. In this case, an effective reconstruction is created by delivering the transformable stent to the site of injury that is identified by cerebral angiography and roadmap guidance. Fluoroscopic radiopaque markers are used, as in Example 1, to identify the site of dissection and allow the accurate delivery of the stent. The stent is delivered in the same manner as in Example 1. Immediately upon deployment, the device is exposed to photon radiation and the transformation of the stent into a more substantial, less porous device begins. Control cerebral angiography is used at the termination of the case to document the repair of the vessel wall segment.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

What is claimed is:

1. A method of treating an aneurysm in a vessel of a patients vasculature comprising the steps of:
    providing a coil delivery system comprising a microcatheter and a coil, wherein the microcatheter comprises a proximal end portion and a distal end portion, and wherein the coil is at least partially coated with a photon-activatable gel material;
    positioning the coil delivery system within the vessel so that the distal end portion of the microcatheter is disposed at a neck of the aneurysm;
    deploying the coil into a cavity of the aneurysm; and
    activating the photon-activatable gel material using an x-ray photon source external to a patient's body, wherein activation of the photon-activatable gel material leads to physical enlargement of the coil within the cavity of the aneurysm thereby isolating the aneurysm from the vessel.

2. The method of claim 1, wherein the distal end portion of the microcatheter further comprises at least one temperature sensor.

3. The method of claim 1, wherein the coil comprises a radiopaque marker.

4. The method of claim 1, further comprising the step of deploying a stent at the neck of the aneurysm.

5. The method of claim 4, wherein the step of deploying the stent further comprises the step of deploying the stent prior to the step of deploying the coil.

6. The method of claim 5, wherein the distal portion of the microcatheter comprises a radiation shielding element.

7. The method of claim 4, wherein the stent further comprises a sidewall and wherein the sidewall of the stent comprises a patch extending on at least a portion of the sidewall of the stent.

8. The method of claim 7, wherein the step of deploying the stent further comprises the step of deploying the stent such that the patch is extending over at least a portion of the neck of the aneurysm.

9. The method of claim 8, wherein the patch is a woven patch.

10. The method of claim 8, wherein the patch is a gel patch.

11. The method of claim 10, wherein the gel patch comprises a radiopaque marker.

12. The method of claim 7, wherein the patch is formed from a coating.

13. The method of claim 7, further comprising activating the patch.

14. The method of claim 13, wherein the step of activating the patch further comprises the step of reducing a size of one or more
  fenestrations of the sidewall of the stent covered by the patch.

15. The method of claim 13, wherein the step of activating the patch further comprises the step of closing one or more interstices of the sidewall of the stent covered by the patch.

16. The method of claim 13, wherein the step of activating the patch further comprises the step of activating the patch to polymerize.

17. The method of claim 13, wherein the step of activating the patch further comprises the step of activating the patch to harden.

18. The method of claim 7, wherein the patch is a photon-activable gel.

19. The method of claim 4, wherein the stent further comprises a sidewall and wherein the sidewall of the stent comprises at least one area
  with a higher density of weaving than another area of the sidewall of the stent.

20. The method of claim 4, further comprising the step of pushing the coil through one or more fenestrations on the sidewall of the stent.

* * * * *